(12) United States Patent
Ahmad et al.

(10) Patent No.: US 8,932,525 B1
(45) Date of Patent: Jan. 13, 2015

(54) THERMAL PIEZOELECTRIC SENSOR FOR CHARACTERIZING ANALYTES IN BREATH AND RELATED METHOD

(75) Inventors: Lubna M. Ahmad, Chandler, AZ (US); Srinivas Tadigadapa, State College, PA (US)

(73) Assignee: Invoy Technologies, LLC, Chandler, AZ (US)

( * ) Notice: Subject to any disclaimer, the term of this patent is extended or adjusted under 35 U.S.C. 154(b) by 0 days.

(21) Appl. No.: 12/482,325

(22) Filed: Jun. 10, 2009

Related U.S. Application Data

(60) Provisional application No. 61/131,809, filed on Jun. 10, 2008.

(51) Int. Cl.
*G01N 15/06* (2006.01)
*G01N 33/00* (2006.01)
*G01N 33/48* (2006.01)

(52) U.S. Cl.
USPC ........... 422/83; 422/50; 422/68.1; 422/82.01; 422/82.02; 422/82.03; 436/43

(58) Field of Classification Search
CPC .......... G01N 27/3271; G01N 33/5438; G01N 27/126; G01N 33/0031; G01N 21/783
USPC ........... 422/50, 68.1, 82.01, 82.02, 82.03, 83; 436/43
See application file for complete search history.

(56) References Cited

U.S. PATENT DOCUMENTS

| | | | | |
|---|---|---|---|---|
| 5,364,797 A * | 11/1994 | Olson et al. | | 436/501 |
| 5,552,274 A * | 9/1996 | Oyama et al. | | 435/6 |
| 5,774,902 A | 7/1998 | Gehse | | |
| 5,866,321 A * | 2/1999 | Matsue et al. | | 435/5 |
| 5,992,215 A * | 11/1999 | Caron et al. | | 73/24.01 |
| 6,106,149 A * | 8/2000 | Smith | | 374/31 |
| 6,189,367 B1 * | 2/2001 | Smith et al. | | 73/19.03 |
| 6,196,062 B1 * | 3/2001 | Wright et al. | | 73/105 |
| 6,370,939 B2 * | 4/2002 | Smith et al. | | 73/19.03 |
| 6,439,765 B2 * | 8/2002 | Smith | | 374/31 |

OTHER PUBLICATIONS

John R. Vigrt, "Uncooled IR Imaging Array Based on Quartz Microresonators", Journal of Microelectromechanical Systems, 1996, pp. 131-137, vol. 5, No. 2.

(Continued)

*Primary Examiner* — Brian J Sines
(74) *Attorney, Agent, or Firm* — Meunier Carlin & Curfman, LLC

(57) ABSTRACT

Described herein is an apparatus for characterizing an analyte in breath and related method. The apparatus comprises an interactant that is configured to interact with the analyte in breath to generate a change in thermal energy relative to a base thermal energy. The apparatus further comprises a piezoelectric system that is coupled to the interactant, comprises at least one piezoelectric material having a material property, and generates a signal that comprises information useful in characterizing the analyte in breath. The signal is in response to a change in a material property of the piezoelectric material. The change in the material property is in response to the change in thermal energy. The apparatus may be used for a variety of applications such as, for example, personal health monitoring, clinical diagnostics, safety and law enforcement monitoring, and others.

30 Claims, 5 Drawing Sheets

(56) References Cited

OTHER PUBLICATIONS

Motoaki Shichiri, "Enhanced, Simplified Glucose Sensors: Long-Term Clinical Application of Wearable Artificial Endocrine Pancreas", Artificial Organs, 1998, pp. 32-42, vol. 22, No. 1, International Society for Artificial Organs, Japan.

Isao Karube, "Microbiosensors", Journal of Biotechnology, 1990, pp. 267-282, vol. 15, Elsevier Science Publishers B.V, Tokyo, Japan.

E. A. Johannessen, "Heat conduction nanocalorimeter for pl-scale single cell measurements", Applied Physics Letters, 2002, pp. 2029-2031, vol. 80, No. 11, American Institute of Physics.

Errol P. Eernisse, "Survey of Quartz Bulk Resonator Sensor Technologies", IEEE Transactions on Ultrasonics, Ferroelectrics, and Frequency Control. 1988, pp. 323-330, vol. 35. No. 3.

Bengt Danielsson, "Calorimetric Biosensors", Journal of Biotechnology, 1990, pp. 187-200, vol. 15, Elsevier, Sweden.

P. Bataillard, "An integrated silicon thermopile as biosensor for the thermal monitoring of glucose, urea and penicillin", Biosensors & Bioelectronics, 1993, pp. 89-98, vol. 8, Elsevier Science Publishers Ltd. Switzerland.

Yuyan Zhang, "Thermal characterization of liquids and polymer thin films using a microcalorimeter", Applied Physics Letters, 2005, pp. 034101-1-034101-3, vol. 86, American Institute of Physics, Pennsylvania.

Yuyan Zhang, "Calorimetric biosensors with integrated microfluidic channels", Biosensors and Bioelectronics, 2004, pp. 1733-1743, vol. 19, Elsevier, Pennsylvania.

Seung-Il Yoon, "*Neisseria meningitidis* Detection Based on a Microcalorimetric Biosensor with a Split-Flow Microchannel", Journal of Microelectromechanical Systems, 2008, pp. 590-598, vol. 17, No. 3, IEEE.

Kumaran Ramanathan, "Principles and applications of thermal biosensors", Biosensors & Bioelectronics, 2001, pp. 417-423, vol. 16, Elsevier Science B.V. Sweden.

\* cited by examiner

THERMAL PIEZOELECTRIC SENSOR FOR CHARACTERIZING ANALYTES IN BREATH AND RELATED METHOD

BACKGROUND

1. Field

The present invention relates to systems, apparatus and methods for characterizing one or more analytes in human breath. Such systems, apparatus and methods may be useful in a variety of applications, for example, such as in personal health monitoring, clinical diagnostics, safety and law enforcement monitoring, and others.

2. Background

A problem facing the medical community is noninvasive disease monitoring and management. Blood analysis is accurate and quantitative, but is invasive, and the pain associated with routine blood sampling leads to low compliance, particularly amongst children and the elderly. Urine analysis, while noninvasive, has been criticized as being inaccurate. Urine analysis is also typically performed using a colorimetric assay, which involves interpretation, and thus poses the problem of being non-quantitative. Thus, these techniques are far from ideal and leave much to be desired.

Low cost, miniature, non-invasive biosensors capable of analyzing small quantities of samples clearly are needed. The need is particularly pronounced for biosensors that are easy to use, have fast response times, and good operational stability, which features are needed in many biochemical and clinical diagnostic applications, such as breath analysis.

Calorimetry is a very powerful and effective investigative tool for analyzing biochemical reactions. Unlike most other biochemical sensors, those based on thermal transducers can be mounted in a protected way that prevents fouling of the base transducer and thereby minimizes the consequential drift in the sensor's response. This provides a significant advantage of operational stability. Also, thermal transducers are not fundamentally limited by the type of interactant (e.g., enzymes, binding agents, etc.) that is used to interact with the analyte of interest to generate a measurement signal. This provides versatility in the interactant used in conjunction with the thermal sensor. Also, the ability to follow the progress of a reaction continuously as a function of time or reactant concentration has many research and clinical applications with far reaching consequences, such as in breath analysis.

Here, we describe a novel form of thermal sensing for breath or related gas analysis.

SUMMARY OF THE INVENTION

In accordance with one aspect of the invention, an apparatus is provided for characterizing an analyte in breath. The apparatus comprises an interactant that is configured to interact with the analyte in breath to generate a change in thermal energy relative to a base thermal energy. The apparatus further comprises a piezoelectric system that comprises at least one piezoelectric material having a material property. The piezoelectric system is coupled to the interactant and the piezoelectric system generates a signal in response to a change in the material property of the piezoelectric material. The change in the material property is in response to the change in thermal energy. The signal comprises information useful in characterizing the analyte in breath.

The apparatus may be or comprise at least one of a chemical reactant, catalyst, polymer, binding agent, phase change agent, adsorbent, absorbent, and vaporization agent. The apparatus may be or comprise a binding agent. The binding agent may be or comprise one of an aptamer and a peptide.

The interactant may be disposed relative to the analyte in breath so that the analyte contacts the interactant via diffusion, convection, or a combination of diffusion and convection.

The piezoelectric system may generate the signal in response to an increase or decrease in thermal energy.

According to another aspect of the invention, the piezoelectric system further comprises an electrode system and a processor, where the processor is operatively coupled to the electrode system.

The piezoelectric system may comprise an array of piezoelectric sensors. The array of piezoelectric sensors may comprise piezoelectric materials that are less than twenty microns in thickness.

The piezoelectric material may be or comprise one of zinc oxide, aluminum nitride, quartz, lithium niobate, lithium tantalate, and relaxor ferroelectrics. The piezoelectric material may comprise a crystallographic orientation where the crystallographic orientation is selected to render the material more sensitive to temperature than the piezoelectric material with a different crystallographic orientation. The crystallographic orientation may be or comprise one of AC-cut, LC-cut, Y-cut, SC-cut, and NLSC-cut.

According to another aspect of the invention, the electrode system may comprise first and second electrodes, and the first electrode may be coupled to the interactant, and the second electrode may not be coupled to the interactant.

The electrode system may comprise first and second electrodes, where both the first and second electrodes contact the piezoelectric material.

The processor may be or comprise a resonator electronic circuit. The resonator electronic circuit may use at least one of single pixel tracking, differential mode tracking, and rf-frequency techniques.

According to another aspect of the invention, the piezoelectric system comprises a first piezoelectric sensor and a second piezoelectric sensor. The first piezoelectric sensor is coupled to the interactant and is configured to generate a first sensor signal. The second piezoelectric sensor is not coupled to the interactant and is configured to generate a second sensor signal. In this embodiment, the piezoelectric system generates the signal as a difference of the first sensor signal and the second sensor signal.

The interactant may be thermally coupled to the piezoelectric system by conductive heat transfer. In this embodiment, the thermal energy may be communicated from the interactant to the piezoelectric system by at least one of the following techniques: self-assembled monolayers, protein sandwich assay techniques, physical dispensation, van der Waal forces, nanomaterials, porous materials, scaffoldings, membranes, traps, and getters. Alternatively, the interactant may be thermally coupled to the piezoelectric system by radiative heat transfer.

The material property may be or comprise a mechanical property of the piezoelectric material and the piezoelectric system may generate the signal in response to a change in the mechanical property. The material property may be or comprise an acoustic wave property of the piezoelectric material and the piezoelectric system may generate the signal in response to a change in the acoustic wave property. The material property may be or comprise a resonance frequency of the piezoelectric material and the piezoelectric system may generate the signal in response to a change in the resonance frequency. The material property may be or comprise a dielectric property of the piezoelectric material and the piezoelectric system may generate the signal in response to a change in the dielectric property.

According to yet another aspect of the invention, the apparatus further comprises a user interface. The user interface displays information useful in characterizing the analyte in breath. The user interface may provide real-time tracking and monitoring of the concentration of the analyte in breath.

The apparatus may further comprise a cavity and the piezoelectric system may be disposed within the cavity. The cavity may be or comprise a hand-held flow conduit, or a facemask.

According to another aspect of the invention, a method is provided for characterizing an analyte in breath. The method comprises providing an interactant and a piezoelectric system operatively coupled to one another, where the piezoelectric system comprises a piezoelectric material. The method further comprises causing the analyte in breath to contact the interactant so that the interactant interacts with the analyte in breath to cause a change in thermal energy. The method further comprises using the piezoelectric system to generate a signal. The signal is in response to a change in a material property of the piezoelectric material. The change in the material property is in response to the change in thermal energy. The signal comprises information useful in characterizing the analyte in breath.

The analyte in breath may be or comprise a constituent of human breath. The constituent of human breath may be or comprise a disease biomarker.

Characterizing the analyte in breath may be or comprise identifying the analyte in breath. Or, it may be or comprise determining the concentration of the analyte in breath. Or, it may be or comprise recognizing a property of the analyte in breath. Or, it may be or comprise a clinical diagnosis.

Providing the interactant may be or comprise providing at least one of a chemical reactant, catalyst, polymer, binding agent, phase change agent, adsorbent, absorbent, and vaporization agent.

Using the piezoelectric system to generate a signal may be or comprise using a resonator oscillator circuit.

Providing the piezoelectric system may be or comprise providing an electrode system and a processor, wherein the processor is operatively coupled to the electrode system.

BRIEF DESCRIPTION OF THE DRAWINGS

The accompanying drawings, which are incorporated in and constitute a part of the specification, illustrate presently preferred embodiments and methods of the invention and, together with the general description given above and the detailed description of the preferred embodiments and methods given below, serve to explain the principles of the invention. Of the drawings.

DETAILED DESCRIPTION OF THE PREFERRED EMBODIMENTS AND METHODS

Figure 1:
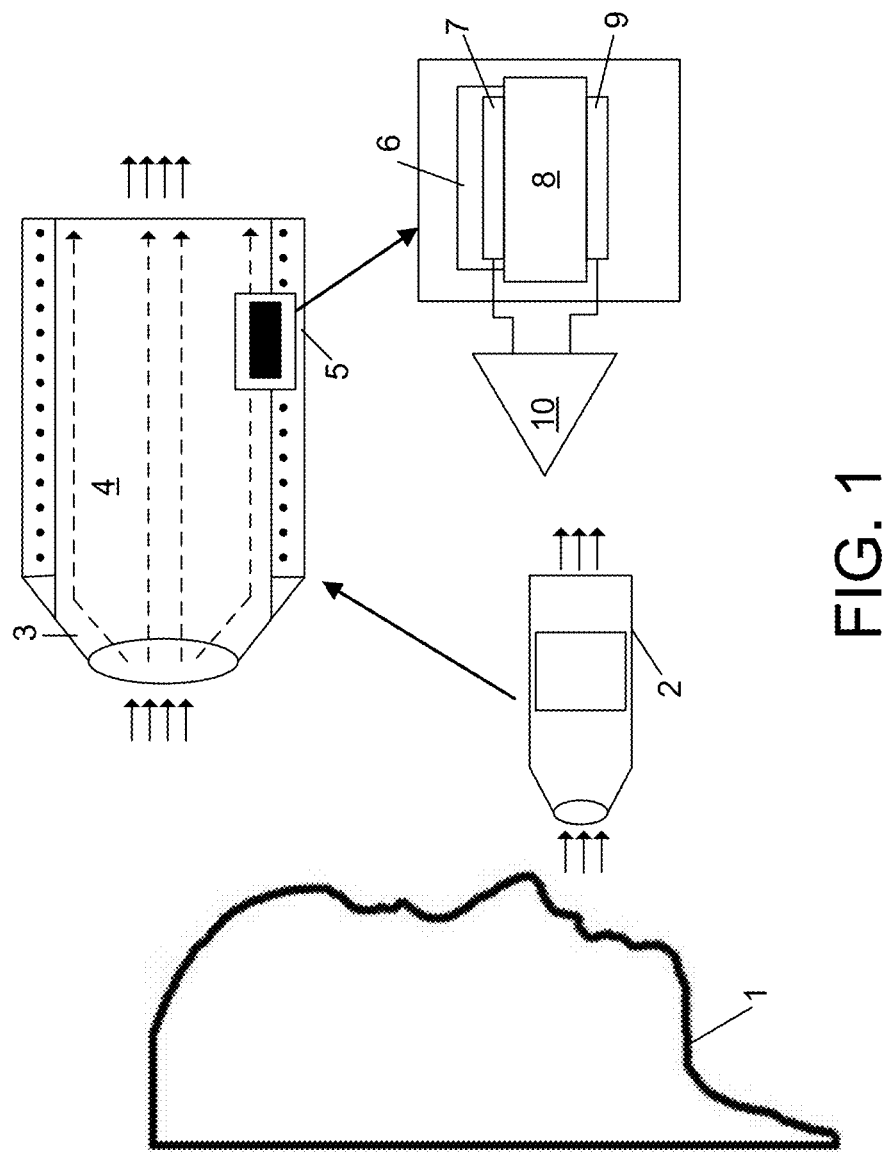
FIG. 1 shows an embodiment of an apparatus for characterizing an analyte in breath, according to an aspect of the invention.

Reference will now be made in detail to the presently preferred embodiments and methods of the invention as illustrated in the accompanying drawings, in which like reference characters designate like or corresponding parts throughout the drawings. It should be noted, however, that the invention in its broader aspects is not limited to the specific details, representative devices and methods, and illustrative examples shown and described in this section in connection with the preferred embodiments and methods. The invention according to its various aspects is particularly pointed out and distinctly claimed in the attached claims read in view of this specification, and appropriate equivalents.

In accordance with one aspect of the invention, an apparatus is provided for characterizing an analyte in breath. An "analyte" as the term is used herein is used according to its common meaning in the field of biochemistry and microbiology, and refers to the chemical component or constituent that is sought to be sensed using devices and methods according to various aspects of the invention. An analyte may be or comprise an element, compound or other molecule, an ion or molecular fragment, or other substance that may be contained within a fluid. In some instances, embodiments and methods, there may be more than one analyte.

The "breath" as referred to herein means the gaseous expiration from the respiration cycle of a human or animal. The invention is advantageously adapted for use in analyzing the exhaled breath of a human being during normal respiration cycles, but may be applied in other circumstances, such as to animals, as well.

The apparatus according to this aspect of the invention comprises an interactant and a piezoelectric system. "Interactant" or "analyte interactant" as the term is used herein is used according to its common meaning in the fields of biochemistry and microbiology, and refers to a substance or system that interacts with the analyte in breath to generate a change in thermal energy. The interactant is configured to interact with the analyte in breath to generate a change in thermal energy of or associated with the piezoelectric system relative to a base thermal energy for that piezoelectric system.

The piezoelectric system is configured to generate a signal that comprises information useful in characterizing the analyte in breath. The piezoelectric system comprises at least one piezoelectric material and it is coupled to an interactant. The interactant interacts with the analyte in breath to generate a change in thermal energy. The extent of the change in thermal energy is related to the concentration of the analyte in breath. This change in thermal energy causes a change in a material property of the piezoelectric material, which generates the signal. In this way, the apparatus may be used in a variety of applications, such as hand-held breath analysis, law enforcement and safety monitors, clinical diagnostics, real-time medical tracking, and others.

There are many instances in which it is desirable to sense the presence and/or quantity of an analyte in breath. "Sense" and "sensing" as the terms are used herein are used broadly to mean detecting the presence of one or more analytes, or measuring the amount or concentration of the one or more analytes.

In accordance with one aspect of the invention, an apparatus is provided for characterizing an analyte in breath. To illustrate this aspect of the invention, an analyte-in-breath sensor 2 according to a presently preferred embodiment of this aspect of the invention is shown in FIG. 1 in conjunction with a patient or other user 1. Although this sensor apparatus could be used in a variety of applications, in this illustrative example it is adapted for use as an acetone sensor for sensing gas or vapor phase acetone in the breath of a human patient or user. Before describing this embodiment in detail, some background on this acetone-sensing application would be useful in appreciating the usefulness of the device and related methods.

Approximately 300 analytes have been identified in human breath. Examples include but are not limited to pentane and other alkanes, isoprene, benzene, acetone and other ketones, alcohols such as ethanol, methanol, isopropanol, ammonia, reflux, medication, and substances which interfere with common alcohol detection systems such as acetaldehyde, acetonitrile, methylene chloride, methyl ethyl ketone, and toluene. Some analytes are in vapor form while others may be in particle form.

Ketone bodies provide a supplementary or substitute form of energy that can be used during various metabolic states including stress, starvation, caloric regulation, or pathology. Breath acetone levels, for example, often are elevated during various metabolic states including stress, starvation, caloric regulation, or pathology such as diabetes and epilepsy. Oftentimes in diabetics, for example, low insulin levels and elevated blood glucose levels result in high concentrations of ketones in the body. This could potentially cause diabetic ketoacidosis ("DKA").

Patients in DKA commonly experience many symptoms such as nausea, fatigue, and rapid breathing. They also emit a fruity odor in their breath, which is distinct and attributable to acetone. Acetone is a volatile ketone body released into alveolar air. If left untreated, DKA can result in coma or even death. However, DKA often is preventable if ketone levels are monitored and treatment is sought when ketone counts are high. The current methods of ketone measurement are blood and urine analysis. The current blood tests typically are accurate, but their invasive nature is undesirable and frequently causes patients to delay treatment. Blood tests also are expensive, as a number of products are needed, including a lancet for blood letting, test strips, a specialized device and batteries. Several studies show that urine analysis is not accurate.

Ketone monitoring also is becoming recognized as a tool for nutritionists or health care professionals to monitor lipid metabolism during dieting. Several studies show that breath acetone concentrations represent lipid metabolism during a calorie deficit. Obesity has become increasingly prevalent and has now reached epidemic levels. It is consequently of great concern to healthcare professionals. Much effort has been invested in treating obesity and promoting healthy weight loss programs for obese individuals. For treatment of obesity, a sensor that measures fat burning would permit patients, doctors and nutrition advisors to adjust weight management plans to individual physiology. A non-invasive, inexpensive, simple-to-use acetone sensor would be an appropriate tool for nutritionists, physicians, and the general public who seek to monitor fat metabolism.

As shown in FIG. 1, in view of this, sensor 2, while merely illustrating presently preferred embodiments and method implementations of various aspects of the invention, is specifically adapted to analyze the breath of a patient or other user 1 to sense the specific analyte acetone in the gas phase that constitutes the user's breath as it is expired into the sensor 2. Moreover, this sensor 2 provides the ability to sense acetone levels in the breath of an individual with relatively high accuracy to aid in assessment and treatment in areas such as those described herein above.

A range of analytes can be sensed using embodiments and method implementations of the invention according to its various aspects. In addition, such embodiments and methods can be used to sense an analyte, or in some cases more than one. Examples of analytes and applications that are amenable to these aspects of the invention include, but are not limited to, the following primary market groups:

(a) Medical devices/nutritional monitors—breath analysis;
(b) Chemical toxicity and/or occupational health and safety compliance—breath analysis for employees who work in an environment where they are inhaling chemicals—e.g., to assess such things as how much are they exhaling, how much is being internalized, whether they are within acceptable limits, etc.;
(c) Law enforcement—e.g., drug or alcohol testing (G-HBA, cannabis, ethanol, etc.); and
(d) Environmental monitoring.

One area of particular interest involves breath analysis. Included among illustrative breath constituents, i.e., analytes, that have been correlated with disease states are those set forth in Table 1, below. As noted, there are perhaps 300 volatile organic compounds that have been identified in the breath, all of which are candidate analytes for analysis using such embodiments and methods. Additionally, in some instances combinations of constituents (analytes) in breath may serve as a superior disease marker relative to the presence of any single analyte.

TABLE 1

| No. | Candidate Analyte | Illustrative Pathophysiology/Physical State |
| --- | --- | --- |
| 1. | Acetone | Lipid metabolism (e.g., epilepsy management, nutritional monitoring, weight loss therapy, early warning of diabetic ketoacidosis), environmental monitoring, acetone toxicity, congestive heart failure, malnutrition, exercise |
| 2. | Ethanol | Alcohol toxicity, bacterial growth |
| 3. | Acetaldehyde | |
| 4. | Ammonia | Liver or renal failure, protein metabolism |
| 5. | Isoprene | Lung injury, cholesterol synthesis, smoking damage |
| 6. | Pentane | Lipid peroxidation (breast cancer, transplant rejection), oxidative tissue damage, asthma, smoking damage, COPD |
| 7. | Ethane | Smoking damage, lipid peroxidation, asthma, COPD |
| 8. | Alkanes | Lung disease, cancer metabolic markers |
| 9. | Benzene | Cancer metabolic monitors |
| 10. | Carbon-13 | *H. pylori* infection |
| 11. | Methanol | Ingestion, bacterial flora |
| 12. | Leukotrienes | Present in breath condensate, cancer markers |
| 13. | Hydrogen peroxide | Present in breath condensate |
| 14. | Isoprostane | Present in breath condensate, cancer markers |
| 15. | Peroxynitrite | Present in breath condensate |
| 16. | Cytokines | Present in breath condensate |
| 17. | Glycans | Glucose measurement, metabolic anomalies (e.g., collected from cellular debris) |
| 18. | Carbon monoxide | Inflammation in airway (asthma, bronchiectasis), lung disease |
| 19. | Chloroform | |
| 20. | Dichlorobenzene | Compromised pulmonary function |
| 21. | Trimethyl amine | Uremia |
| 22. | Dimethyl amine | Uremia |
| 23. | Diethyl amine | Intestinal bacteria |
| 24. | Methanethiol | Intestinal bacteria |

TABLE 1-continued

| No. | Candidate Analyte | Illustrative Pathophysiology/Physical State |
|---|---|---|
| 25. | Methylethylketone | Lipid metabolism |
| 26. | O-toluidine | Cancer marker |
| 27. | Pentane sulfides | Lipid peroxidation |
| 28. | Hydrogen sulfide | Dental disease, ovulation |
| 29. | Sulfated hydrocarbon | Cirrhosis |
| 30. | Cannabis | Drug concentration |
| 31. | G-HBA | Drug testing |
| 32. | Nitric oxide | Inflammation, lung disease |
| 33. | Propane | Protein oxidation, lung disease |
| 34. | Butane | Protein oxidation, lung disease |
| 35. | Other Ketones (other than acetone) | Lipidpid metabolism |
| 36. | Ethyl mercaptane | Cirrhosis |
| 37. | Dimethyl sulfide | Cirrhosis |
| 38. | Dimethyl disulfide | Cirrhosis |
| 39. | Carbon disulfide | Schizophrenia |
| 40. | 3-heptanone | Propionic acidaemia |
| 41. | 7-methyl tridecane | Lung cancer |
| 42. | Nonane | Breast cancer |
| 43. | 5-methyl tridecane | Breast cancer |
| 44. | 3-methyl undecane | Breast cancer |
| 45. | 6-methyl pentadecane | Breast cancer |
| 46. | 3-methyl propanone | Breast cancer |
| 47. | 3-methyl nonadecane | Breast cancer |
| 48. | 4-methyl dodecane | Breast cancer |
| 49. | 2-methyl octane | Breast cancer |
| 50. | Trichloroethane | |
| 51. | 2-butanone | |
| 52. | Ethyl benzene | |
| 53. | Xylene (M, P, O) | |
| 54. | Styrene | |
| 55. | Tetrachloroethene | |
| 56. | Toluene | |
| 57. | Ethylene | |
| 58. | Hydrogen | |

Examples of other analytes would include bromobenzene, bromochloromethane, bromodichloromethane, bromoform, bromomethane, 2-butanone, n-butylbenzene, sec-butylbenzene, tert-butylbenzene, carbon disulfide, carbon tetrachloride, chlorobenzene, chloroethane, chloroform, chloromethane, 2-chlorotoluene, 4-chlorotoluene, dibromochloromethane, 1,2-dibromo-3-chloropropane, 1,2-dibromoethane, dibromomethane, 1,2-dichlorobenzene, 1,3-dichlorobenzene, 1,4-dichlorobenzene, dichlorodifluoromethane, 1,1-dichloroethane, 1,2-dichloroethane, 1,1-dichloroethene, cis-1,2-dichloroethene, trans-1,2-dichloroethene, 1,2-dichloropropane, 1,3-dichloropropane, 2,2-dichloropropane, 1,1-dichloropropene, cis-1,3-dichloropropene, trans-1,3-dichloropropene, ethylbenzene, hexachlorobutadiene, 2-hexanone, isopropylbenzene, p-isopropyltoluene, methylene chloride, 4-methyl-2-pentanone, methyl-tert-butyl ether, naphthalene, n-propylbenzene, styrene, 1,1,1,2-tetrachloroethane, 1,1,2,2-tetrachloroethane, tetrachloroethene, toluene, 1,2,3-trichlorobenzene, 1,2,4-trichlorobenzene, 1,1,1-trichloroethane, 1,1,2-trichloroethane, trichloroethene, trichlorofluoromethane, 1,2,3-trichloropropane, 1,2,4-trimethylbenzene, 1,3,5-trimethylbenzene, vinyl acetate, vinyl chloride, xylenes, dibromofluoromethane, toluene-d8, 4-bromofluorobenzene.

Embodiments and methods according to these aspects of the invention may be employed to measure disease markers in the breath, where either elevated or low levels may be important for diagnostic purposes. As noted above, for example, diabetic ketoacidosis (DKA) is a condition where ketone levels in the body are abnormally high. Hyperosmolar non-ketotic syndrome is a condition where ketone levels in the body are subnormal, meaning that the body is not producing enough ketone bodies for normal functioning. While in some embodiments the sensor may be employed to measure changes in analyte concentrations in a fluid, it is not limited to this and can measure absolute concentrations instead or as well.

It is important to note that devices according to various aspects of the invention can be used to measure the concentration of multiple analytes simultaneously. By use of multiple piezoelectric sensors, for example, an entire screening can be performed with one breath.

The apparatus for characterizing an analyte in breath comprises an interactant, as noted herein above. The interactant is configured to interact with the analyte in breath to generate a change in thermal energy. As was explained above, the interactant can comprise any substance or system for interacting with the analyte in breath to generate a change in thermal energy. Examples include such substances as a chemical reactant, catalyst, polymer, vapochromic materials, binding agent (such as an aptamer or a peptide), phase change agent, adsorbent, absorbent, vaporization agent, or combinations thereof.

Although the list of candidate analyte interactants provided here is not necessarily exhaustive, presently preferred analyte interactants would include those described herein, and others as well. "React" as the term is used herein includes not only chemical reaction, but other forms of reaction in which the state of the analyte and/or analyte interactant, their properties or state, or the properties or state of their environment is changed. Examples of reaction regimes might include, for example, physical or chemical absorption or adsorption, physical or chemical reaction, Van der Waals interactions, transitions that absorb or release thermal energy, and the like.

In one example, the interactant is activated carbon that adsorbs acetone. In this example, the interactant is a part of an apparatus that is used to measure breath acetone levels for applications like diabetes and dietary fat loss monitoring.

Interactants can consist of or comprise adsorbents, including but not limited to activated carbon, silica gel, and platinum black. Preferably, the adsorbent can be impregnated with another species that reacts with the analyte following the adsorption. While interactants may be or comprise adsorbents or absorbents, as may be appreciated, they are not limited to them.

Interactants also can consist of or comprise chemicals or chemical reactants. Suitable chemicals that interact with acetone include but are not limited to halogenated compounds, sodium hypochlorite, hypochlorous acid, sodium monochloroisocyanurate, sodium dichloroisocyanurate, monochloroisocyanuric acid, dichloroisocyanuric acid, and trichloroisocyanuric acid. Alcohol can interact with a chemicals such as chromium trioxide ($CrO_3$) or enzymes such as alcohol dehydrogenase, alcohol oxidase, or acetoalcohol oxidase. Other reactants may be or comprise chloroform, chloroform in the presence of a base, and nitrosyl chloride.

Ammonia is a very important analyte. Breath ammonia is found in elevated concentration in patients with renal or liver failure. If ammonia were the analyte in the gas, ammonia can react with many different substances. As an example, ammonia reacts with hydrochloric acid to form ammonium chloride. The ammonium chloride will subsequently react with barium hydroxide to form barium chloride, ammonia, and water. This will allow for a two-step reaction sequence thereby increasing the total enthalpy of the reaction producing an amplification of the enthalpy.

Optionally, the interactant may not directly interact with the analyte in breath, but a byproduct of the interactant and some other compound in the gas can produce a different interactant with which the analyte in breath reacts. A possible reason for selecting such an interactant is for stability. Thus, if the true analyte-interacting species is unstable under the particular operating conditions, then it may be desirable to select a more stable interactant that, upon exposure to the analyte or some other substance present in the gas containing the analyte, produces a different analyte interactant. For example, trichloroisocyanuric acid can react with water to form hypochlorous acid, which engages in an enthalpic reaction with acetone.

Vapor phase reactions are sometimes limited because reactions in aqueous solution typically involve acid or base catalysis. Therefore, in the vapor phase, the presence of a catalyst or an activating agent, such as a protonating agent, may be critical to allow the interactant and analyte to interact.

Optionally, interactants also can be or comprise hydrogenation reagents. For acetone, Raney nickel and platinum catalysts are suitable interactants.

The volatile organic compound can also interact with materials from living systems or living systems themselves. Examples include but are not limited to microorganisms, cells, cellular organelles and genetically modified versions thereof. These living systems engage in metabolic processes to sustain life, which involve energy exchange and therefore heat consumption or generation. Some chemical analytes such as toxins or pathogens kill or damage cells or impair organelle function. If the living material is immobilized on the sensing junctions of a thermopile, therefore, the change in heat generated or consumed is related to the number of living cells, which can be related to the presence of a toxin or pathogen.

Optionally, the interactant may be selected such that the interaction with the volatile organic compound involves interaction with other substances in the gas, such as water, oxygen, or another analyte.

While not wishing to be limited to any particular mechanism or theory of operation, the thermal energy change sensed at the thermopile device in some cases may comprise heats of condensation. "Phase change agents" can perform a number of functions relevant to latent heat energy. For example, they can facilitate evaporation and/or condensation. With regard to condensation, they can alter the surface area such that there is more or less condensation over the sensor; and promote increased (or decreased) condensation based on the phase change agent's properties, for example, increasing condensation may occur over phase change agents that have a greater polarity.

Candidate interactants that may be useful in presently preferred embodiments and method implementations according to various aspects of the invention include organometallic vapochromic materials, such as [Au2Ag2(C6F5)4(phen)2]n. These types of materials are powders at room temperature, which make them easy to deposit, and react with volatile organic compounds, such as acetone, in the gas-phase. These materials are designed to change color upon exposure to a particular analyte, which color-change causes a change in thermal energy.

The interactant may also be regenerative. Examples of regenerative interactants may include interactants that are true catalysts. Or, regenerative interactants may be interactants that can be regenerated (after they are consumed or partially consumed) by use of a refilling gas stream. For instance, particularly for living or polymeric interactants, interactants may become more reactive when exposed to water. In such instances, water may be used to regenerate the immobilized analyte interactant after it has been consumed or partially consumed by exposure to the analyte. Referring once more to polymeric interactants, while analyte interactants may be or comprise polymers, they are not limited to them.

The interactant may be immobilized on the sensing portion of the piezoelectric system directly. If, however, the interactant can cause corrosion or other negative impacts to the piezoelectric material that will affect the longevity of the device, other embodiments may be better suited. Preferably, the interactant is immobilized on a strip that is adhered tightly with the piezoelectric material atop the electrode.

For this type of sensor system, the ideal chemical reactant typically is regenerative (not consumed), highly selective to the analyte of interest, and non-toxic, has a long shelf life, and engages in a highly exothermic or endothermic reaction with the analyte or analytes.

More than one interaction can also occur simultaneously or sequentially. This can occur if multiple interactants are immobilized on the sensing portion of the piezoelectric system. Alternatively, the product or intermediary, etc. of a first reaction may initiate a set of secondary reactions, which may or may not involve the analyte. In any case, the net enthalpy of these interactions will make up the change in thermal energy. A non-zero net enthalpy causes a change in thermal energy, which change in thermal energy can be quantified by the piezoelectric system.

Even if only one interaction occurs, the chemistry may be selected such that the products of the initial reaction act as reactants during secondary interactions with the analyte or other substances which can amplify temperature changes.

In other cases, measuring multiple analytes is desirable. In the presently preferred embodiments, each piezoelectric sensor within the array is coated with a different interactant such that selectivity of several analytes is determined by the different interactions. The response of the individual piezoelectric sensors is determined by the individual sensor output, which creates an overall profile. This profile or pattern will be characteristic of a specific analyte or analytes of similar chemical family and can therefore be used to identify at least one analyte.

Thus, a single analyte interactant may be used to sense one or more analytes. This is useful, for example, when a single analyte interactant senses a class of analytes. Or, multiple analyte interactants can be used to sense a single analyte very specifically. Or, multiple analyte interactants can be used to sense multiple analytes (e.g., for screening purposes).

The interactant can be disposed relative to the analyte in breath so that the analyte contacts the interactant in a number of different ways. For example, the analyte can contact the interactant via diffusion, convection, or a combination of diffusion and convection. The analyte in breath passes over the interactant in a laminar fashion so as to minimize the turbulence in the flow stream. Alternatively, if maximal mass transfer to the surface must be achieved, high velocities, and thus turbulent flow, may be desired, depending on the application. The flow regime is, in many cases, application-specific.

The interactant is configured to interact with the analyte in breath to generate a change in thermal energy relative to a base thermal energy. The term "base thermal energy" is intended to be construed broadly. For example, it may or may not be time varying, or a steady value. To clarify this, consider that the overall base thermal energy of the apparatus or a component thereof may be varying with time. This lack of constancy in the base thermal energy may be useful to the operation of the apparatus (e.g., for parametric amplification) or it may be imposed by the environment (e.g., due to ambient temperature fluctuations). In any case, the change in thermal energy is relative to this base thermal energy, and the change may be or comprise an increase, a decrease, or a combination thereof, depending on the specific situation.

The apparatus for characterizing a volatile organic compound comprises a piezoelectric system. The piezoelectric system comprises a piezoelectric material having a material property, is coupled to the interactant, and generates a signal that comprises information useful in characterizing the analyte in breath. The signal is in response to a change in a material property of the piezoelectric material. The change in the material property is in response to the change in thermal energy, where the change in thermal energy is in response to the interaction of the analyte in breath and the interactant.

Figure 2:
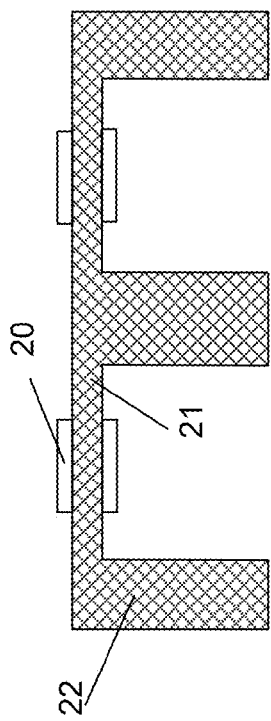
FIG. 2 shows a presently preferred embodiment of a piezoelectric system according to an aspect of the invention.

FIG. 2 shows an example of a piezoelectric system. In this embodiment, the piezoelectric system comprises a piezoelectric material 16, a first electrode 15, and a second electrode 17.

There are a number of piezoelectric materials that can be employed in various embodiments and methods according to this aspect of the invention. For instance, synthetic (e.g. polymers such as poly(vinylidene fluoride) or PVDF) and natural (e.g., minerals and ionic crystals) materials can be used. Some examples of piezoelectric materials would include: zinc oxide, aluminum nitride, quartz, lithium niobate, lithium tantalite, relaxor ferroelectrics, non-polar crystals, polar crystals, etc. It should be understood that other materials or combination of materials that exhibit appropriate piezoelectricity may be a candidate for use.

Preferably, the piezoelectric material comprises a crystallographic orientation wherein the crystallographic orientation renders the material more sensitive to temperature than the piezoelectric material with a different crystallographic orientation. Examples of crystallographic orientation are AC-cut, LC-cut, Y-cut, SC-cut, and NLSC-cut. Also preferably, a material property of the piezoelectric material, such as dielectric properties or the resonance frequency, is highly temperature sensitive or more temperature sensitive than other properties.

The sensor may also be made from a monolithic piezoelectric crystal, or as a hybrid or integrated device on and from different substrate materials.

In a presently preferred embodiment, the piezoelectric system further comprises an electrode system and a processor, where the processor is operatively coupled to the electrode system. The term "electrode system" is to be construed broadly, in that the piezoelectric system may be configured with appropriate electrodes or electrical access, and the electrical access may be via physical connection or through some other means, such as via electromagnetic transmission. For instance, possible embodiments of the sensor system can include remotely actuated configurations in which the piezoelectric crystal is driven and monitored through the use of appropriate frequency radio waves. This may allow, for example, for the interactant to the disposed directly on the piezoelectric material, instead of atop the electrode system.

In understanding different configurations of the electrodes, there are a few noteworthy points. Preferably, the electrodes are in intimate contact with the piezoelectric material. Commonly, conductive metals, such as gold and copper, are used. However, other materials may be used as well.

Referring to FIG. 2, the first electrode 15 is coupled directly to the interactant and the second electrode 17 is not be coupled to the interactant. Alternatively, both electrodes 15 and 17 are coupled to the interactant, but only the interactant on the first electrode 15 is exposed to the analyte in breath. In a different embodiment, the first electrode 15 is coupled to a first interactant and the second electrode 17 is coupled to a second interactant. Accordingly, there are different ways that the electrode system is coupled to the interactants. Also, as already mentioned herein, there are presently envisioned embodiments in which the interactant is not disposed on the electrode system, but rather directly on the piezoelectric system.

Figure 3:
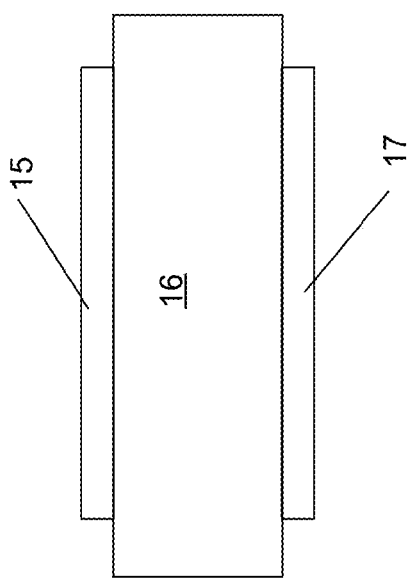
FIG. 3 shows a presently preferred embodiment of a micromachined piezoelectric system that provides good thermal isolation and with low thermal mass, according to an aspect of the invention.

FIG. 3 shows another embodiment of a piezoelectric system, which is a micromachined piezoelectric system for good thermal isolation and with low thermal mass. The piezoelectric material 22 is etched to form a cavity 21 below the sensing area. The sensing area has two electrodes 20. In this embodiment, there are two sensing elements and a total of four electrodes. Micromachining the piezoelectric crystals for the realization of the sensor can help to create regions of low thermal mass and thermal conductance to act as the sensing element.

As those skilled in the art will appreciate, decreasing the thermal mass and increasing the thermal isolation of a thermal transducer generally aids in decreasing the noise and improving the signal. Some techniques for fabricating a thermal transducer with low mass and high thermal isolation are described in the literature.

There are a number of specific piezoelectric system designs that can be incorporated into the design of presently preferred embodiments and method implementations according to the invention. The specific design employed in a particular breath analysis apparatus will be suited to the particular application, design requirements, constraints, etc. Examples of piezoelectric systems that may be used advantageously in such systems include those based on a quartz microresonator, for example, such as adaptations of those described for IR sensing applications in Vig et. al., "Uncooled IR Imaging Array Based on Quartz Microresonators," 1996 *Journal of Microelectromechanical Systems*, pgs. 131-136, June 1996, which is incorporated herein by reference, or adaptations of the chemical and biological sensors based on microresonators as are provided in U.S. Pat. No. 5,774,902, issued to Vig on Apr. 28, 1998, which is incorporated herein by reference. Another illustrative approach would be a piezoelectric system based on an adaptation of a Y-cut quartz resonator for liquid-phase acid base neutralization reactions as is described in Tadigadapa et. al., "Y-cut Quartz Resonator based Calorimetric Sensor," IEEE 2005 in Irvine, Calif., which is also incorporated herein by reference.

Having described the basic components of illustrative sensor 2, an illustration of a preferred implementation of a method for its operation in accordance with another related aspect of the invention will now be described. With reference to FIG. 1, a user 1 blows into mouthpiece 3. The breath passes through the mouthpiece 3 into cavity 4 where the piezoelectric system 5 comprising a piezoelectric material 8 is located. The piezoelectric system also comprises two electrodes 7 and 9, which are in intimate contact with the piezoelectric material 8. An interactant 6 is coupled to the first electrode 7. The analyte in the breath diffuses to or otherwise contacts the surface of the interactant 6 where it reacts with it in an enthalpic process. The heat generated or consumed from this process is transferred to the piezoelectric material 8, thereby raising or lowering the temperature of the piezoelectric material. This heat generation or consumption causes a change in a material property of the piezoelectric material, such as resonance frequency. The change in this material property is registered by a processor 10, which generates a signal that contains information useful in characterizing the analyte in breath. From this signal and the embodied thermal energy change, an assessment may be made as to whether the analyte-analyte interactant reaction involved acetone as the analyte. It also may be used to assess the amount and/or concentration of the acetone analyte in the gas stream.

The design details of the piezoelectric system 5 can vary, and can be optimized to meet different needs or design objectives. For example, the piezoelectric material may be cut in a rectangular or circular shape, as suited for the particular application. The circular embodiment may be preferred in systems, for example, where the interactant is best immobilized as a droplet or other spherical form.

Preferably, a piezoelectric system comprises an array of piezoelectric sensors. A simple embodiment of an array of piezoelectric sensors is shown in FIG. 3. In this embodiment, there are two piezoelectric sensors; however, in other embodiments, an increased number of sensors are used. In some instances, a chip contains nearly one hundred piezoelectric sensors. Piezoelectric sensors refer to the piezoelectric material coupled to an electrode or with appropriate electrical access, though this is not intended to be limiting. Some other mechanism for measuring the output of the piezoelectric material may be used.

As stated earlier, piezoelectric sensors may be linked in arrays. Several piezoelectric sensors can have the same interactant to detect the same analyte. Their outputs could be averaged by a processor with the result that net effect of noise is reduced. Alternatively, the various piezoelectric sensors may be connected in series and the net output transmitted to a microprocessor. Alternatively, each of several piezoelectric sensors may be coated with a different interactant so as to more selectively detect an analyte.

If multiple devices are used either to more selectively identify the analyte or to reduce the error of a single device, then there are some geometry considerations that may be important. For instance, the devices could all be placed side by side as close to the leading edge as possible. If this is not possible or desirable under the circumstances, then the devices could be placed with gaps between them. The exact geometry can vary from one setup to the next. One may place the devices in a chess-board like pattern because the formation of the boundary layer is streamline-specific.

One embodiment of the piezoelectric system involves the use of a bulk acoustic resonator, which comprises a piezoelectric crystal. In this example, there are two opposing metal electrodes sandwiching and in intimate contact with a piezoelectric crystal. The bulk acoustic resonator has high temperature sensitivity of the resonance frequency.

As stated earlier herein, the piezoelectric system may, and preferably does, comprise a processor. Preferably, the processor is coupled to the electrode system. The processor may be any apparatus that is capable of processing the output of the piezoelectric material and generating a signal. For example, the processor may be or comprise a microcontroller, a microprocessor, or a radio-frequency generator/receiver coupled to the piezoelectric system.

The output of the piezoelectric device 5 can be measured directly or by use of this processing device 10. The processing device may report the raw signal or may convert the raw signal to a concentration or other interpretable signal. This conversion may be programmed by use of a calibration curve, look-up table, or other method.

Optionally, the processing device may be used to provide feedback, which feedback can be programmed to analyze the status and transmit commands to operate similar to a drug delivery device.

The processor may comprise a resonator electronic circuit. In this case, the processor may use single pixel tracking, differential mode tracking, or rf-frequency techniques to analyze the output of the piezoelectric material.

As may be appreciated from this description, the sensor may be used in a wide variety of implementations and methods. Moreover, the sensor may be used in conjunction with different components that may, for example, aid in the regulation, interpretation, and/or maintenance of the environment and conditions surrounding analysis. As such, the sensor or processing unit (e.g., microprocessor, microcontroller) may be required to process a substantial amount of information. As such, it may be desirable to test a variety of different signal interpretation methods to determine a reliable indicator of analyte concentration or presence.

The output of the piezoelectric sensor may be analyzed in a number of ways, including the peak-to-peak difference, maximum value, minimum value, slope of the curve, area under the curve, time to reach certain points, steady state values, etc. Different methods may be employed to determine these features. For example, the area under the curve may be computed using the Trapezoid Rule or the Midpoint Rule. Or, the slope may be computed using, for example, ten data points or one hundred data points, depending on the situation.

Additionally, combinations of such features and interactions of such features can be considered. For example, if the steady state value is above value=X, then the peak to peak difference ought to be interpreted according to method Y. Alternatively, if the area under the curve=X, this means that the flow rate=Y and if the flow rate=Y, then the peak-to-peak difference can be scaled by factor Z to more accurately predict the concentration of the analyte. These are mere examples; others of course may be implemented depending on the components, signal, circumstances, conditions of analysis, analyte-analyte interactant interaction, etc.

In addition to the output of the piezoelectric sensor, other factors may also be considered. For example, the processor may need to consider the output of multiple piezoelectric sensors, which are coated with the same analyte interactant. In this instance, the processor may average the outputs or it may discard outliers prior to analysis. In other instances, the processor may need to consider the output of multiple piezoelectric sensors each of which is coated with a different analyte interactant. This may affect the processing algorithm. For example, perhaps the processor interprets the output of piezoelectric sensor #2 to mean that the concentration of analyte #2 is X; the processor may then interpret the output of piezoelectric sensor #5 accounting for fact that the concentration of analyte #2 is X.

In analyzing the signal, the processor may also need to account for the output of components other than the piezoelectric sensor. For example, the processor may be coupled to a flow measuring device, an ambient temperature gage, a filtering unit, or a combination of components. In such instances, the algorithm for signal interpretation may be more complex and involve multiple steps.

Additionally, the processor may be coupled to buttons or some type of user interface. In such instances, user preferences may, in part, dictate the output of the device. For example, if the user inputs the ambient temperature, the presence of interfering substances in his or her breath, a certain disease state, a certain error tolerance or required specificity, etc, the processor may elect certain algorithms to use in the analysis of the data received.

Figure 4:
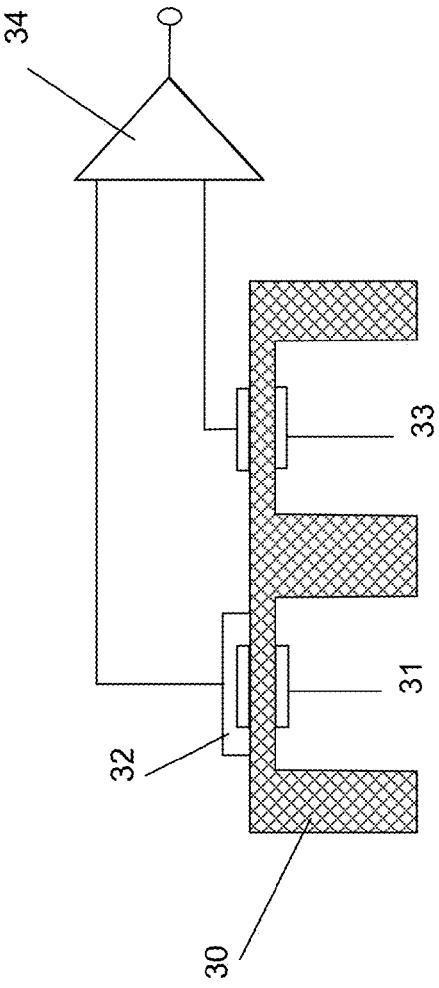
FIG. 4 shows a presently preferred embodiment of a piezoelectric system in differential mode according to an aspect of the invention.

FIG. 4 shows an embodiment of a piezoelectric system that operates in differential mode. In this embodiment, the micro-machined piezoelectric material 30 has two sensing elements 31 and 33. Sensing element 31 is functionalized with an interactant 32. The second sensing element 33 is not functionalized. The two sensing elements are coupled to a processor 34 that compares the output of sensing element 31 to the output of sensing element 33. The processor further generates information useful in characterizing the volatile organic compound.

When the breath expired by the patient passes over the sensor, the piezoelectric material may experience a non-interaction based temperature change merely due to the fact that expired breath is close to body temperature, which is close to 37° C. If the material is originally contained in an environment, which is at 37° C. or some equilibrated temperature, this may not be an issue. To compensate for this type of an issue, a piezoelectric system that operates in differential mode may be desired so as to cancel non-interaction thermal effects.

Referring again to dual-mode operation, preferably but optionally, both the reference piezoelectric sensor 33 and sensing piezoelectric sensor 31 are first coated with a non-interactive substance (with respect to the analyte) that helps to equalize the thermal load on both of these junction sets. For example, if an enzyme such as alcohol dehydrogenase is entrapped within a gel matrix, the gel matrix without the enzyme might be placed on the reference junctions and that gel containing the enzyme on the sensing junctions. In another case, both the reference and sensing junctions are coated with a substance like silicone grease. Over the sensing junctions, the silicone grease adheres interactants that are in particle form, such as trichloroisocyanuric acid. This may help to normalize the response of the materials.

The apparatus may comprise a calorimetric bulk acoustic wave sensor configured in differential mode with one sensor functionalized to give the calorimetric signal and the other without functionalization. This configuration may help to decrease common mode drift, mass loading, viscous effect based response, and noise signals thereby resulting in higher signal to noise performance figure of merit.

The apparatus for characterizing an analyte in breath may further comprise a second transducer system. The second transducer system provides a second signal that comprises information useful in characterizing the analyte in breath. Examples of a second transducer system include, but are not limited to, a thermopile, an electrochemical sensor, a mass-sensitive sensor, an optical sensor, etc. A combination device may help to overcome the limitations of a single transducer.

The interactant may be thermally coupled to the piezoelectric system in a number of ways. For example, the interactant may be thermally coupled using a technique that facilitates radiative heat transfer. Or, the interactant may be coupled using a technique that facilitates conductive heat transfer so that the thermal energy is communicated from the interactant to the piezoelectric system. Examples of techniques that may be used include, but are not limited to, self-assembled monolayers, protein sandwich assay techniques, physical dispensation, van der Waal forces, nanomaterials, porous materials, scaffolding, membranes, traps, getters, and a combination thereof.

The interactant preferably is disposed directly on one of the electrodes that sandwich the piezoelectric material. However, the interactant may, in certain embodiments, be disposed on a test strip, where the test strip comes in contact with the electrodes. The test strip may serve as a barrier to heat transfer, but if it is sufficiently thin, this may still be acceptable.

Preferably, the interactant is patterned in a manner so as to maximize the flux of the analyte in breath to the surface. One way to increase the flux of analyte at and to the surface is to interrupt the growth of the concentration boundary layer. If the analyte interactant is immobilized in a discontinuous fashion such that the interactant is immobilized for a certain distance and followed thereafter by some degree of interruption, then the concentration boundary layer thickness will decay. The interruption may include but is not limited to a non-reactive surface of the same or a greater distance as the adjacent region of analyte interactant. Thereafter, if analyte is present at the surface, the concentration boundary layer will begin to grow again. In this way, the flux of analyte to the surface can be maintained relatively high at each point where there is analyte present. Using this manner of chemical patterning, the flux to the surface of analyte can greatly surpass the flux that would be achieved if the entire surface had been coated with interactant without such interruptions and discontinuities. Different ways of generating interruptions may be used.

As stated earlier herein, the piezoelectric system generates a signal in response to change in a material property of the piezoelectric material. The change in the material property is in response to the change in thermal energy.

The material property may be or comprise a mechanical property of the piezoelectric material, such as the Young's modulus. Or, it may be or comprise an acoustic wave property, or a dielectric property. Preferably, the material property is the resonance frequency of the piezoelectric material.

The piezoelectric system generates a signal and the signal comprises information useful in characterizing the analyte in breath. Characterizing the analyte may involve identifying the analyte, determining the concentration of the analyte, recognizing a property of the analyte, etc.

The characterization can be quantitative or qualitative, depending on the application, use, design objectives, etc. For example, an acetone sensor designed for pediatric patients may be equipped with colored indicators that correlate with the seriousness of diabetic ketoacidosis. However, for physicians, the exact concentration of acetone may be displayed.

The apparatus for characterizing the volatile organic compound may comprise a user interface. This user interface may be used to communicate information to or from the piezoelectric system. For example, the interface may display the information useful in characterizing the analyte, such as the real-time tracking of the concentration of acetone in the breath of a diabetic patient. Or, the interface may include a button for an individual to input the surrounding ambient temperature, for use in calibrating the device.

The apparatus for characterizing the volatile organic compound may comprise a cavity within which the piezoelectric system is disposed. This cavity may, for example, be a hand-held flow conduit or a face-mask.

As an example, the breath may be captured by a face mask (which may be of standard gas mask design or some other) and is then directed through a polyethylene tube where it is then filtered by a particle filter. The breath is directed by the tubing to a distendable volume that is well-stirred by fan or other method. The flow of the breath through a channel that leads to a chamber containing the sensor can be controlled by a valve that leads to the ambient environment.

In this example, the distendable volume would allow for well-mixed fluid to enter the channel in a regulated, laminar flow manner. As a result, variations in patient breath such as flow velocity patterns, interfering substances, temperature gradients, and particulate matter would be controlled, normalized, and mixed prior to introduction to the sensor inside chamber. This is useful, for instance, because the first volume of expired air may be non-physiologically active (i.e., lung dead space).

In this environment, the sensor could be used for continuous monitoring of patients. Suitable, well-known, electronics could be used to communicate with nurses' stations, hospital computers or set of local alarms.

The interactant is in fluid communication with the cavity in the sense that the interactant is positioned relative to the cavity so that the breath received into the cavity contacts the interactant so that the desired or anticipated analyte-interactant reaction can occur. Preferably, the interactant is positioned within the cavity or conduit so that at least a portion of the breath entering the cavity or conduit is caused or permitted to contact and react with the interactant. Alternative designs, however, are possible. An example would comprise placing the interactant at an exit orifice of the cavity or outside of but immediately adjacent to a portion of the cavity.

The piezoelectric system can be integrated within a microfluidic gas analysis device. Microfluidic devices have gained significant interest recently due to their ability to perform multiple processes in very short time intervals and in very little space. The piezoelectric system is well suited for use in a microfluidic gas analyzer because it can be miniaturized.

Sensors according to the various aspects of the invention may be used in conjunction with supplementary or disposable/refillable components. For example, the sensor may be used with a software package that stores results of the sensor, a calibration unit, disposable/refillable cartridges of analyte interactant, or disposable filters.

Such sensors may also be used with disposable or refillable cartridges of analyte interactant. For instance, a test strip may be inserted into the device, said test strip containing some of the analyte interactant. These test strips may be used more than once or may be designed for single use only. Additionally, the test strips may contain multiple analyte interactants or single analyte interactants. Also, the test strips may contain interactants that complement interactants that are already on the sensor, e.g., to increase specificity and/or sensitivity.

Such sensors may be used with disposable filters. These filters may be or comprise bacterial filters, moisture filters, or filters for interfering substances.

The sensor 2 can be used in conjunction with a software package that could, via a USB cable or the like, store either the entire signal from the thermopile device or selected features therefrom. These values can be synthesized into a progress report, which may periodically be sent to a medical practitioner. Based on the progress report, the program can make suggestions for medication, lifestyle, or other changes.

A method for characterizing an analyte in breath comprises three steps, which are not necessarily in this order. The method comprises providing a piezoelectric system, which comprises a piezoelectric material, and an interactant, which is coupled to the piezoelectric system. The method further comprises causing the analyte in breath to contact the interactant so that the interactant interacts with the analyte in breath to cause a change in thermal energy. The method further comprises using the piezoelectric system to generate a signal, where the signal is as described herein.

EXAMPLE 1

Shear-mode quartz resonators made from certain crystal cuts can be used as very sensitive temperature sensors. Table 2 lists the temperature sensitivity of the resonance frequency as a function of temperature for different quartz crystal cuts, according to Vig et. al., "Uncooled IR Imaging Array Based on Quartz Microresonators," 1996 *Journal of Microelectromechanical Systems*, pgs. 131-136, June 1996, which is incorporated herein by reference. This phenomenological sensitivity of quartz crystals represents 1-3 orders of magnitude improvement in temperature sensitivity in comparison to other similar temperature dependent phenomena such as the Seebeck effect on which a thermopile device is based or thermistor. Thus, quartz crystal resonators can be configured as high performance thermal sensors.

TABLE 2

Temperature dependence of the resonance frequency of different cuts of quartz.

| Quartz Crystal Cut | Temperature Dependence of the Resonance Frequency (ppm/° C.) |
|---|---|
| AC-Cut | 20 |
| LC-Cut | 35.4 |
| Y-Cut | 90 |
| SC-Cut (b-mode) | −25.5 |
| SC-Cut (dual mode) | 80-100 |
| NLSC-Cut | 14 |

To improve the sensitivity of the calorimeter, use of temperature sensitive cuts of quartz (for example Y-cut with a temperature coefficient of frequency change ~90 ppm/° C.) is proposed for the detection of volatile organic compounds in human breath. The phenomenological temperature sensitivity of Y-cut quartz represents 1-3 orders of magnitude improvement in temperature sensitivity as compared to other temperature dependent phenomena such as Seebeck effect on which a thermopile device is based. This temperature sensitivity along with the low noise performance that can be achieved in quartz crystal oscillators provides a high level of sensitivity, which is one advantage of these sensing elements in breath analysis.

The temperature profile of the Y-cut resonator pixel can be modeled as a circular membrane (pixel) of radius $\alpha$, and of uniform thickness d. The electrode (resonator) area will be smaller than the pixel area for energy confinement and quality factor reasons. Neglecting radiation and convection heat losses and assuming uniform heat generation $\dot{Q}$ per unit time per unit area over the whole pixel area, the radial temperature profile of the quartz membrane can be modeled by the two dimensional heat conduction equations. If the boundaries of the circular quartz membrane are assumed to be clamped at ambient temperature, the solution of the heat conduction equation can be written as follows, according to Carslaw, H. S, and Jaeger, J. C., "Conduction of Heat in Solids" Oxford: Oxford University Press, 1959.

$$\Delta T(r)|_{Membrane} = \frac{\dot{Q}(a^2 - r^2)}{4\kappa_\| d}$$

where $\Delta T(r)$ is the temperature difference between the pixel membrane at radius r and the rim of the membrane and $\kappa_\|$ is the planar thermal conductivity for the membrane material. The average temperature over the electrode area which covers the membrane from r=0 to r=a/2 can be given by $\Delta T(r)|_{avg} = 11\dot{Q}a^2/48\kappa_\| d$, where $\kappa_\|$ for Y-cut quartz is 1.38 Wm$^{-1}$K$^{-1}$.

For the sake of understanding the model, an example of a piezoelectric thermal sensor is provided using a model urea system. It is important to note, however, that this model may be applied to measurement of acetone or other analytes in human breath. In fact, use of this model may be used to help optimize the performance of the detector. Assuming the heat generated on the surface of the membrane is due to an enzymatic reaction, the heat generated per unit time per unit area can be calculated using the expression $\dot{Q}=\Delta H.M.d_c/\tau$, where $\Delta H$ is the enthalpy of the reaction in J/mol, M is the molarity of the reactant in moles/liter, $d_c$ is the depth of the reaction chamber, and τ is the time, in seconds, required to refresh the entire volume of the reaction chamber which in turn depends on the flow rate used in the experiment. For the case of catalytic hydrolysis of urea molecules using urease, 1 M solution of urea will generate a total heat of $6.1 \times 10^7$ J/m$^3$ of heat when completely reacted. For the typical flow rates used in the enzymatic testing, τ=0.27 s. Using the depth of the reaction chamber of 30 μm, the heat generated per unit area per second on the membrane can be estimated to be $6.8 \times 10^3$ W/m$^2$.

Figure 5:
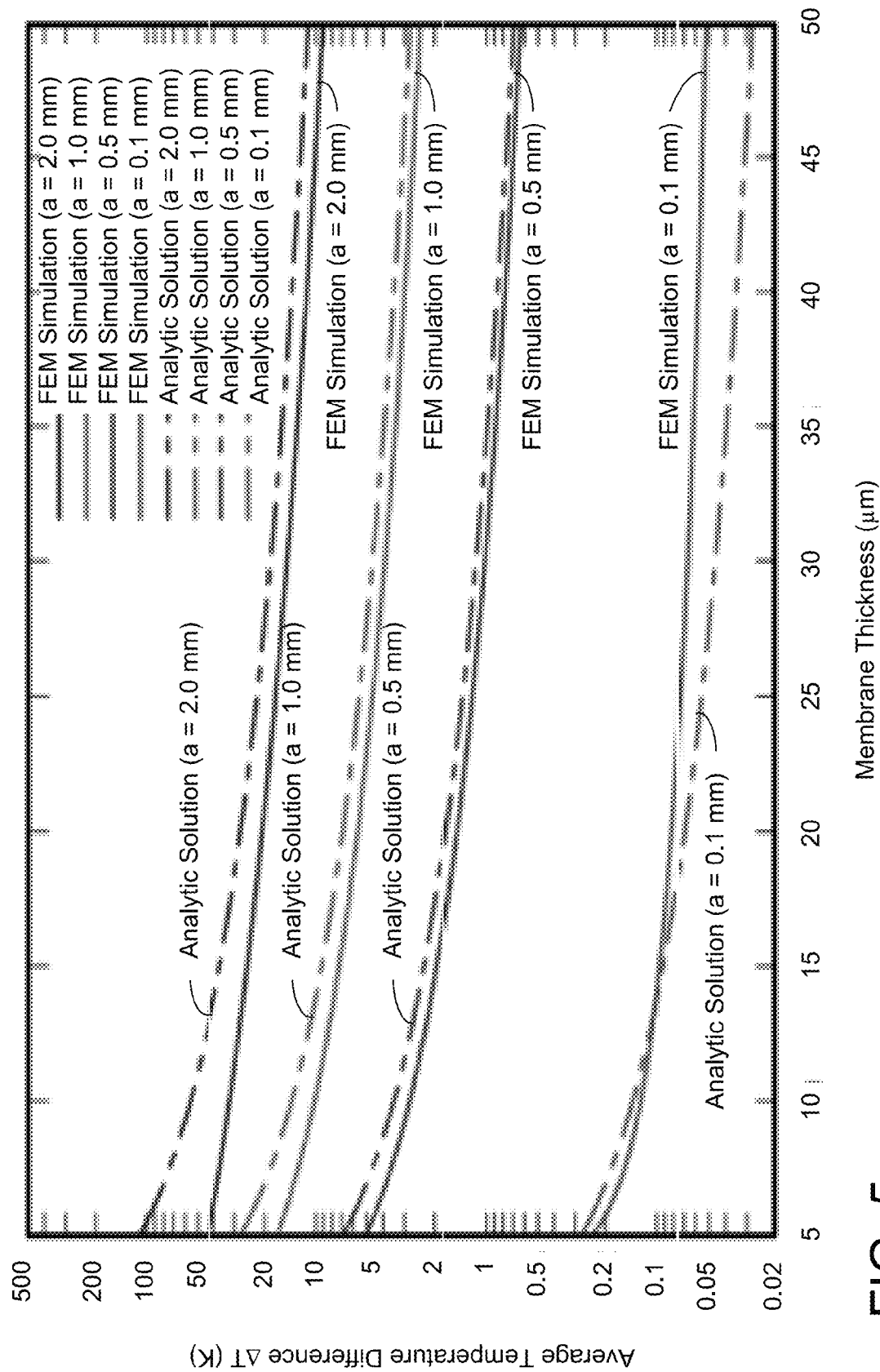
FIG. 5 shows a graph of the average electrode temperature increase for different membrane diameter and thickness for the hydrolysis of 1M of urea for an embodiment of a thermal piezoelectric system tested in a laboratory setting.

Using this value of $\dot{Q}$, the average temperature, $\Delta T(r)|_{avg}$, was calculated and plotted as a function of membrane thickness for different pixel diameters and is shown in FIG. 5. From this it can be concluded that for a 25 μm thick quartz pixel of 1 mm diameter (with electrode diameter of 500 μm), the average increase in the temperature of the quartz membrane is ~10° C. for completely reacted 1 M urea solution. Assuming a temperature resolution of $10^{-4}$° C. using the quartz resonator, the expected sensitivity of the device is ~10 μM (250 femtomoles) for a sample volume of ~25 nl. The proposed technique has the potential of at least 1-3 orders of sensitivity improvement over existing calorimetric sensors.

EXAMPLE 2

Figure 6:
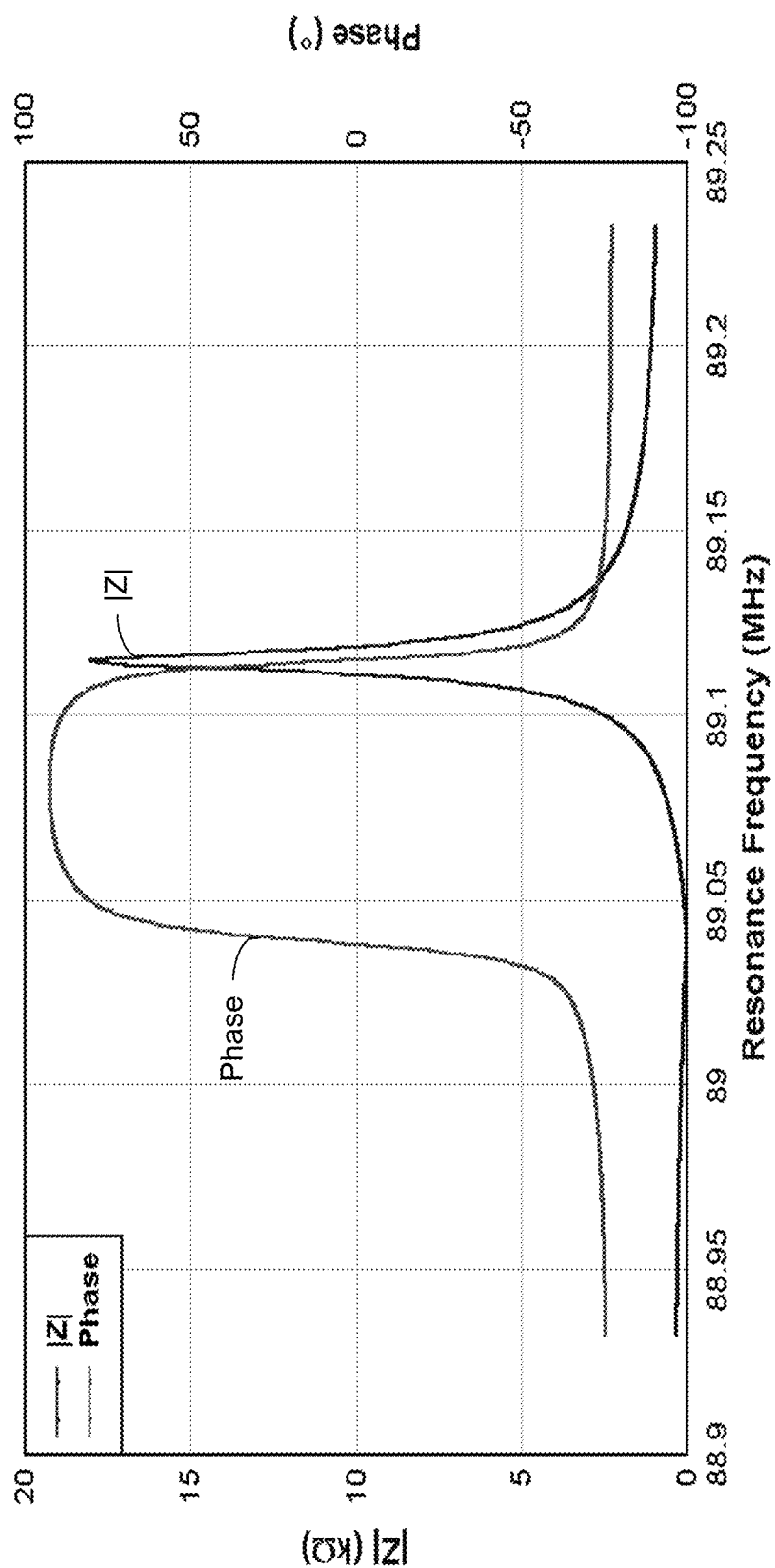
FIG. 6 shows a graph of the typical impedance characteristic of an 89-Hz Y-cut quartz pixel at resonance for an embodiment of a thermal piezoelectric system.

Y-cut quartz resonator arrays with pixel size of 1 mm diameter and pixel thickness of 18.5 μm have been fabricated. Using an impedance analyzer coupled with a multiplexer, four pixels were simultaneously monitored for their performance. The impedance spectrum of the 89 MHZ Y-cut quartz resonator is shown in FIG. 6.

Figure 7:
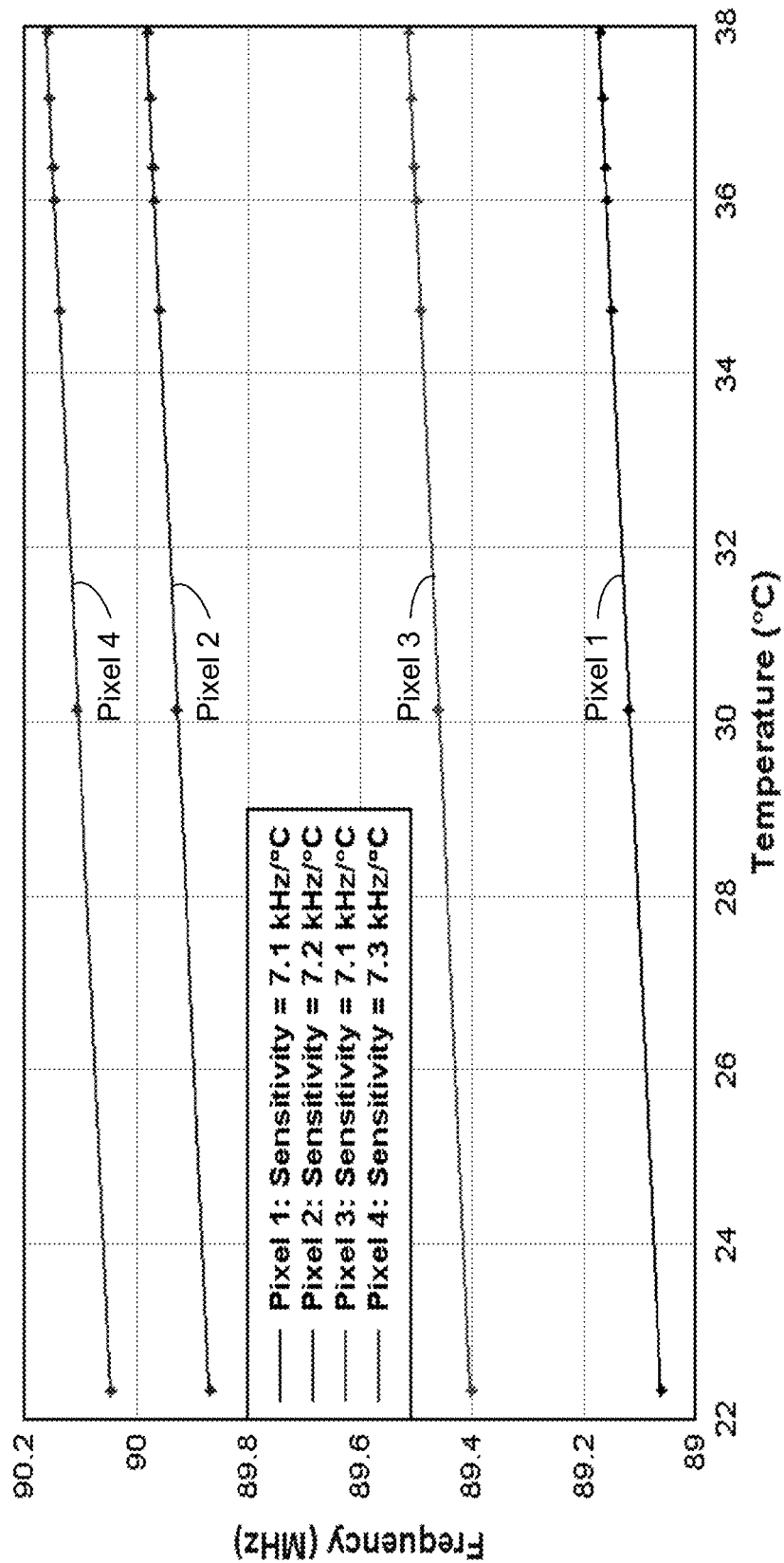
FIG. 7 shows a graph of the temperature sensitivity of a Y-cut quartz resonator array around room temperature for an embodiment of a thermal piezoelectric system.

The fabricated resonator array was then calibrated for temperature sensitivity in an oven. The temperature inside the oven was monitored using two thermocouples, one mounted on the walls of the oven and the other located in close proximity to the resonator in the center of the oven. Calibration was performed over the temperature range of room temperature to ~38° C. Frequency calibration at higher temperatures was not investigated because, for the intended applications, the calorimeter is expected to monitor reactions which produce small amounts of heat and the overall temperature of the resonator is not expected to go beyond ~38° C. FIG. 7 shows a graph of the temperature sensitivity of a Y-cut quartz resonator array around room temperature. This implies a frequency sensitivity of ~81 ppm, which is close to, the expected value of 90 ppm listed in literature. The typical noise level of the resonator was ~10-15 Hz implying a temperature resolution of ~2 mK.

Especially for the measurement of certain breath biomarkers, a sensor with a high level of sensitivity is advantageous. The resolution of the piezoelectric thermal sensor cited above can be dramatically improved in a number of ways, including those that follow, for breath analysis. One way to improve the sensitivity is to decrease the thickness of the piezoelectric material, in this case, the quartz pixel, to, for example, ~20 μm, or even ~5 μM or less. This will help in at least two ways. If the resonance frequency is the material property sought to be used, the resonance frequency of the quartz will increase, thereby improving the resolution. Also, the thermal mass will decrease, which will improve the thermal/heat transfer characteristics of the material. Other methods may be used to improve the thermal isolation and reduction of thermal mass of the sensor to optimize its calorimetric performance.

Another way to improve the sensitivity is by decreasing the noise or improving the frequency stability level from 10-15 Hz to 1-5 Hz or lower.

Another way to improve the sensitivity is by changing the material from quartz to another material, such as lithium niobate, which may exhibit improved performance.

As stated herein, in certain instances, the sensitivity of the measurements can also be improved by performing measurements in a differential sensing mode.

As the temperature resolution improves, it may be desirable to cool the piezoelectric material or the overall apparatus to take advantage of the high sensitivity.

Additional advantages and modifications will readily occur to those skilled in the art. Therefore, the invention in its broader aspects is not limited to the specific details, representative devices and methods, and illustrative examples shown and described. Accordingly, departures may be made from such details without departing from the spirit or scope of the general inventive concept as defined by the appended claims and their equivalents.

What is claimed is:

1. An apparatus for characterizing an analyte in breath, the apparatus comprising:
   a) a mouthpiece;
   b) an interactant that is configured to interact with the analyte in breath to generate a change in thermal energy relative to a base thermal energy; and
   c) a piezoelectric system comprising at least one piezoelectric material having a material property, wherein the piezoelectric system further comprises a processor, the processor comprising a resonator electronic circuit, the processor operatively coupled to the piezoelectric system, wherein the piezoelectric system is coupled to the interactant, and further wherein a change of thermal energy in the piezoelectric material is registered by the processor, which generates a thermal energy signal, wherein the thermal energy signal is used to characterize the analyte in breath.

2. An apparatus as recited in claim 1, wherein the interactant comprises at least one of a chemical reactant, catalyst, polymer, binding agent, phase change agent, adsorbent, absorbent and vaporization agent.

3. An apparatus as recited in claim 1, wherein the interactant comprises a binding agent, and wherein the binding agent comprises at least one of an aptamer and a peptide.

4. An apparatus as recited in claim 1, wherein the interactant is disposed relative to the analyte in breath so that the analyte contacts the interactant via diffusion.

5. An apparatus as recited in claim 1, wherein the interactant is disposed relative to the analyte in breath so that the analyte contacts the interactant via a combination of diffusion and convection.

6. An apparatus as recited in claim 1, wherein the interactant is disposed relative to the analyte in breath so that the analyte contacts the interactant via convection.

7. An apparatus as recited in claim 1, wherein the piezoelectric system generates the signal in response to an increase in the thermal energy.

8. An apparatus as recited in claim 1, wherein the piezoelectric system generates the signal in response to a decrease in thermal energy.

9. An apparatus as recited in claim 1, wherein the piezoelectric system further comprises an electrode system, wherein the processor is operatively coupled to the electrode system.

10. An apparatus as recited in claim 1, wherein the piezoelectric system comprises an array of piezoelectric sensors.

11. An apparatus as recited in claim 1, wherein the at least one piezoelectric material comprises at least one of zinc oxide, aluminum nitride, quartz, lithium niobate, lithium tantalite and relaxor ferroelectrics.

12. An apparatus as recited in claim 10, wherein the array of piezoelectric sensors comprises piezoelectric materials that are less than twenty microns in thickness.

13. An apparatus as recited in claim 1, wherein the piezoelectric material comprises a crystallographic orientation, and wherein the crystallographic orientation of the piezoelectric material is selected to render the material more sensitive to temperature than the piezoelectric material with a different crystallographic orientation.

14. An apparatus as recited in claim 13, wherein the crystallographic orientation is one of AC-cut, LC-cut, Y-cut, SC-cut, and NLSC-cut.

15. An apparatus as recited in claim 9, wherein the electrode system comprises first and second electrodes, the first electrode is coupled to the interactant, and the second electrode is not coupled to the interactant.

16. An apparatus as recited in claim 9, wherein the electrode system comprises first and second electrodes, and the first and second electrodes contact the piezoelectric material.

17. An apparatus as recited in claim 1, wherein the resonator electronic circuit includes at least one of single pixel tracking, differential mode tracking, and rf-frequency techniques.

18. An apparatus as recited in claim 1, wherein the piezoelectric system comprises
   a) a first piezoelectric sensor that is coupled to the interactant and which is configured to generate a first sensor signal, and,
   b) a second piezoelectric sensor that is not coupled to the interactant and which is configured to generate a second sensor signal; and the piezoelectric system generates the signal as a difference of the first sensor signal and the second sensor signal.

19. An apparatus as recited in claim 1, wherein the interactant is thermally coupled to the piezoelectric system by conductive heat transfer.

20. An apparatus as recited in claim 19, wherein the interactant is thermally coupled to the piezoelectric system so that the thermal energy is communicated from the interactant to the piezoelectric system by at least one of self-assembled monolayers, protein sandwich assay techniques, physical dispensation, van der Waal forces, nanomaterials, porous materials, scaffoldings, membranes, traps and getters.

21. An apparatus as recited in claim 1, wherein the interactant is thermally coupled to the piezoelectric system by radiative heat transfer.

22. An apparatus as recited in claim 1, wherein the material property comprises a mechanical property of the piezoelectric material, and the piezoelectric system generates the signal in response to a change in the mechanical property.

23. An apparatus as recited in claim 1, wherein the material property comprises an acoustic wave property of the piezoelectric material, and the piezoelectric system generates the signal in response to a change in the acoustic wave property.

24. An apparatus as recited in claim 1, wherein the material property comprises a resonance frequency of the piezoelectric material, and the piezoelectric system generates the signal in response to a change in the resonance frequency.

25. An apparatus as recited in claim 1, wherein the material property comprises a dielectric property of the piezoelectric material, and the piezoelectric system generates the signal in response to a change in the dielectric property.

26. An apparatus as recited in claim 1, further comprising a user interface wherein the user interface displays the information useful in characterizing the analyte in breath.

27. An apparatus as recited in claim 26 wherein the user interface provides real-time tracking and monitoring of the concentration of the analyte in breath.

28. An apparatus as recited in claim 1, further comprising a cavity, wherein the piezoelectric system is disposed within the cavity.

29. An apparatus as recited in claim 28, wherein the cavity comprises a hand-held flow conduit.

30. An apparatus as recited in claim 28, wherein the cavity comprises a facemask.

\* \* \* \* \*